United States Patent [19]

Kabbe

[11] 4,415,741

[45] Nov. 15, 1983

[54] CHROMAN-4-ONES AND PROCESS FOR PREPARING SAME

[75] Inventor: Hans-Joachim Kabbe, Leverkusen, Fed. Rep. of Germany

[73] Assignee: Bayer Aktiengesellschaft, Leverkusen, Fed. Rep. of Germany

[21] Appl. No.: 337,802

[22] Filed: Jan. 7, 1982

Related U.S. Application Data

[63] Continuation of Ser. No. 853,932, Nov. 22, 1977, abandoned, which is a continuation of Ser. No. 706,098, Jul. 16, 1976, abandoned.

[30] Foreign Application Priority Data

Aug. 7, 1975 [DE] Fed. Rep. of Germany ....... 2535338
Mar. 20, 1976 [DE] Fed. Rep. of Germany ....... 2611910

[51] Int. Cl.³ ............................................ C07D 311/22
[52] U.S. Cl. ...................... 549/345; 549/401; 549/344; 549/332; 549/60; 549/13; 549/9; 549/408; 548/409; 546/17; 260/239 B
[58] Field of Search ...................... 260/345.2, 239 B; 549/401, 345, 344, 332, 60, 13, 9; 568/409; 546/17

[56] References Cited

U.S. PATENT DOCUMENTS 3,699,128 10/1972 Strandtmann et al. ............ 549/401

*Primary Examiner*—Nicky Chan
*Attorney, Agent, or Firm*—Sprung, Horn, Kramer & Woods

[57] ABSTRACT

Chroman-4-ones are prepared by reacting an o-hydroxyarylcarbonyl compound with a carbonyl compound in the presence of an amine. A typical reaction of o-hydroxy-acetophenone with cyclopentanone can be depicted as follows:

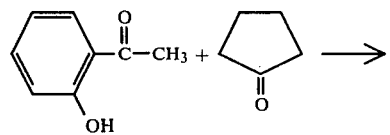

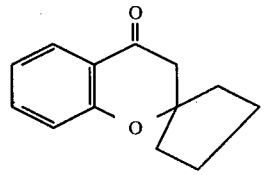

11 Claims, No Drawings

CHROMAN-4-ONES AND PROCESS FOR PREPARING SAME

This is a continuation of application Ser. No. 853,932 filed Nov. 22, 1977 (now abandoned) which in turn is a continuation of Ser. No. 706,098 filed July 16, 1976 (now abandoned).

BACKGROUND

This invention relates to a process for the preparation of chroman-4-ones, and to chroman-4-ones produced thereby.

It is known to prepare 2-aryl-chroman-4-ones by reacting benzaldehydes with o-hydroxyacetophenones. A disadvantage of this process is that mixtures of different compounds are formed and that the reaction takes up to 83 days (Elderfield, Heterocyclic Compounds, volume 2, page 347).

Furthermore, chroman-4-ones can be prepared by the reaction of phenols with α,β-unsaturated carboxylic acid chlorides and subsequent rearrangement of the reaction product (Bull. Soc. Chem. Belge 82, 705 (1973)). A disadvantage of this process is the use of a large excess of polyphosphoric acid, which cannot be re-used.

It is also possible to prepare chroman-4-ones by cyclisation of β-aryloxypropionic acids in the presence of a Friedel-Crafts catalyst (European Journal of Medicinal Chemistry, 1975, 257). Large amounts of the Friedel-Crafts catalyst, the removal of which is involved and gives rise to pollution of the environment, are necessary in order to carry out this process.

SUMMARY

According to the invention there is now provided a process for the preparation of chroman-4-ones of the formula

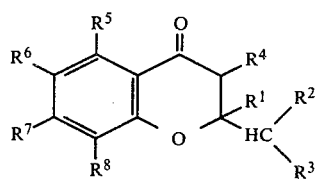

wherein
$R^1$ to $R^4$ are identical or different and represent hydrogen or optionally substituted alkyl, alkenyl, cycloalkyl, cycloalkenyl, aryl, aralkyl, alkoxycarbonyl, carboxyl or aminoalkyl and
$R^2$ to $R^4$ also represent amino or dialkylamino and
wherein
$R^1$ and $R^2$ can be closed to form a carbocyclic or heterocyclic ring and
$R^5$ to $R^8$ are identical or different and represent hydrogen, halogen, hydroxyl, nitro, cyano, carboxyl or optionally substituted alkyl, cycloalkyl, aryl, aralkyl, alkoxy, aralkoxy, aryloxy, alkoxycarbonyl, amino, alkylamino, dialkylamino or acylamino,
in which o-hydroxy-arylcarbonyl compounds of the formula

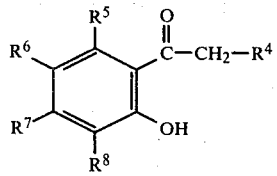

wherein
$R^4$ to $R^8$ have the abovementioned meaning,
are reacted with carbonyl compounds of the formula

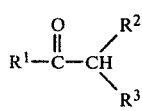

wherein
$R^1$ to $R^3$ have the abovementioned meaning,
in the presence of amines of the formula

wherein
$R^{19}$ and $R^{10}$ represent alkyl groups which, together with the N atom, can be linked to form a heterocyclic ring.

DESCRIPTION

The process according to the invention can be illustrated with the aid of the following reaction equation for the reaction of o-hydroxy-acetophenone with cyclopentanone;

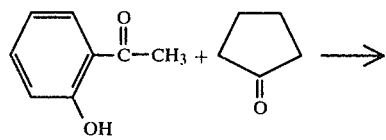

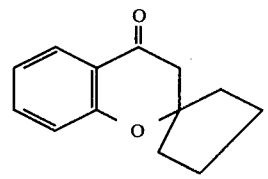

Optionally substituted alkyl and alkenyl radicals ($R^1$ to $R^8$) which may be mentioned are straight-chain or branched radicals with up to 18, preferably up to 12 and particularly preferentially up to 6, carbon atoms. It is also possible for the alkenyl radicals to contain several, preferably up to four, double bonds. Examples of alkyl and alkenyl radicals which may be mentioned are: methyl, ethyl, propyl, isopropyl, butyl, isobutyl, tert.-butyl, hexyl, nonyl, decyl, undecyl, octadecyl, but-3-enyl, 4-methylpent-3-enyl, 4,8-dimethylnona-3,7-dienyl and 4,8,12-trimethyltrideca-3,7,11-trienyl.

Examples of possible substituted cycloalkyl radicals ($R^1$ to $R^8$) are those with 3 to 18, preferably with 4 to 12 and particularly preferentially with 5 and 6, carbon atoms, such as, for example, cyclopropyl, cyclobutyl, cyclopentyl, cyclohexyl, cycloheptyl, cyclooctyl, cyclododecyl, cycloheptadecyl and cyclooctadecyl, preferably cyclopentyl and cyclohexyl. Possible optionally substituted cycloalkenyl radicals are cyclic radicals with the same number of carbon atoms, preferably 5-membered and 6-membered alicyclic radicals which have a double bond, such as cyclopentenyl, cyclohex-3-enyl and 4-methylcyclohex-3-enyl.

Optionally substituted aryl radicals ($R^1$ to $R^8$) which may be mentioned are those with 6 to 14 carbon atoms, such as phenyl, naphthyl and anthracyl, preferably phenyl.

Examples of possible optionally substituted aralkyl radicals ($R^1$ to $R^8$) are those which have 7 to 18 carbon atoms and in which the aliphatic part contains 1 to 8, preferably 1 to 4, carbon atoms and the aromatic part represents a carbocyclic radical with 6 to 10 carbon atoms. The following aralkyl radicals may be mentioned as examples: benzyl, phenylethyl, phenylpropyl, phenylbutyl, naphthylmethyl and naphthylethyl, preferably benzyl.

If $R^1$ and $R^2$ are linked together with the formation of an optionally substituted ring, the latter can be both carbocyclic and heterocyclic.

Examples of possible carbocyclic rings ($R^1/R^2$) are saturated or unsaturated rings containing hydrocarbon members, preferably 3-membered to 12-membered rings. It is also possible for the carbocyclic rings to be fused to one or more radicals of the benzene series.

Examples of carbocyclic radicals which may be mentioned are: cyclopropane, cyclopentane, cyclohexane, cycloheptane, cyclooctane, cyclononane, cyclodecane, cycloundecane, cyclododecane, cyclohexene, cyclooctene, cyclododecene and tetralin.

Possible heterocyclic rings ($R^1/R^2$) are, for example, 5-membered to 12-membered rings, preferably 5-membered and 6-membered rings, which, in addition to hydrocarbon members, also contain one or more heteroatoms, such as, for example, nitrogen, oxygen and/or sulphur. The heterocyclic rings can contain 1 or 2 double bonds and can also be fused to one or more radicals of the benzene series. Examples of heterocyclic radicals which may be mentioned are: piperidine, pyrrolidine, tetrahydrofurane, tetrahydropyrane and tetrahydrothiopyrane.

If the radicals $R^9$ and $R^{10}$, which are joined to NH in the formula (IV), form a ring, this can be, for example: pyrrolidine, piperidine, morpholine and N-methyl-piperazine.

The alkyl and aryl radicals of the alkoxy, alkoxycarbonyl, alkylamino, dialkylamino, aryloxy and aralkoxy radicals have, in respect of the number of carbon atoms contained therein, the same range of meanings as indicated above.

Preferred alkoxy groups which may be mentioned are those with up to 4 carbon atoms, such as methoxy, ethoxy, propoxy, isopropoxy, butoxy, isobutoxy and tert.-butoxy.

Preferred aryloxy groups which may be mentioned are those with 6 or 10 carbon atoms, such as phenoxy and naphthoxy.

Preferred aralkoxy groups which may be mentioned are those with 7 to 10 carbon atoms, such as benzyloxy, phenylethoxy, phenylpropoxy, phenylisopropoxy, phenylbutoxy, phenylisobutoxy and phenyl-tert.-butoxy.

Preferred alkoxycarbonyl groups which may be mentioned are those with up to 4 carbon atoms in the alkyl radical, such as methoxycarbonyl, ethoxycarbonyl, propoxycarbonyl, isopropoxycarbonyl and butoxycarbonyl.

Preferred alkylamino and dialkylamino groups which may be mentioned are those with up to 3 carbon atoms in the alkyl radical, such as methylamino, ethylamino, propylamino, isopropylamino, dimethylamino, diethylamino, dipropylamino and diisopropylamino. It is also possible for the two alkyl radicals of the dialkylamino group to be closed to form a ring, such as, for example, pyrrolidinyl and piperidinyl.

The acylamino group ($R^5$ to $R^8$) can be substituted by an aliphatic or aromatic radical, the aliphatic radical and the aromatic radical having the abovementioned range of meanings. Examples of acylamino groups which may be mentioned are: formylamino, acetylamino, propionylamino, valcroylamino and benzoylamino.

Halogens which may be mentioned are fluorine, chlorine, bromine and iodine, preferably bromine and chlorine.

Possible substituents of the alkyl, cycloalkyl, aryl, aralkyl, alkoxy, aralkoxy, alkoxycarbonyl, alkylamino and dialkylamino groups of the radicals $R^1$ to $R^8$ are substituents which are not changed under the reaction conditions. Examples which may be mentioned are the halogens, such as fluorine, chlorine, bromine and iodine, the cyano group, the $C_1$–$C_6$-alkyl group, the $C_1$–$C_6$-alkoxy group, the $C_1$–$C_6$-alkoxycarbonyl group, the $C_1$–$C_6$-alkoxycarbonylalkyl group, the amino group, the $C_1$–$C_6$-alkylamino group and the $C_1$–$C_6$-dialkylamino group, aryl radicals from the benzene series or the carboxylic acid group.

Preferred o-hydroxy-aryl-carbonyl compounds of the formula II, which can be employed according to the process of the invention, are compounds of the formula

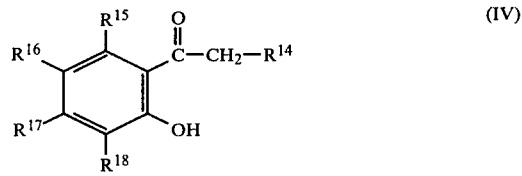

(IV)

wherein $R^{14}$ represents hydrogen, $C_1$ to $C_6$ alkyl, phenyl, naphthyl, $C_7$ to $C_9$ aralkyl or $C_2$ to $C_6$ dialkylamino and $R^{15}$ to $R^{18}$ are identical or different and represent hydrogen, chlorine, bromine, hydroxyl, $C_1$ to $C_6$ alkyl, phenyl, $C_1$ to $C_6$ alkoxy, $C_7$ to $C_9$ aralkoxy, phenyloxy, amino, $C_2$ to $C_6$ dialkylamino or $C_1$ to $C_7$ acylamino.

The o-hydroxy-aryl-carbonyl compounds which can be used for the process according to the invention are known (Beilstein, volume VIII, 85 et seq.).

Examples which may be mentioned are: o-hydroxyacetophenone, 3-chloro-2-hydroxyacetophenone, 5-chloro-2-hydroxyacetophenone, 2,6-dihydroxy-4-(N)-pyrrolidinylacetophenone, 2,4-dihydroxyacetophenone, 2,5-dihydroxyacetophenone, 2,6-dihydroxyacetophenone, 2,3-dihydroxyacetophenone, 2,4,6-trihydroxyacetophenone, 4-pentyl-2,6-dihydroxyacetophenone, 4-heptyl-2,6-dihydroxyacetophenone, 4-(1',1'-dimethylphenyl)-2,6-dihydroxyacetophenone, 3,4-dimethoxy-6-methyl-2,5-dihydroxyacetophenone, 3,4,6-trimethyl-2,5-dihydroxyacetophenone, 3-methoxy-2-hydroxyacetophenone, 4-methoxy-2-hydroxyacetophenone, 5-methoxy-2-hydroxyacetophenone, 6-methoxy-2-hydroxyacetophenone, 4-benzyloxy-2-hydroxyacetophenone, 5-benzyloxy-2-hydroxyacetophenone, 4-acetylamino-2-hydroxyacetophenone, 5-acetylamino-2-hydroxyacetophenone, 4-phenoxy-2-hydroxyacetophenone, 4-cyclohexyl-2-hydroxyacetophenone, 5-phenyl-2-hydroxyacetophenone, 3-β-phenylethyl-2-hydroxyacetophenone, 5-δ-phenylbutyl-2-hydroxyacetophenone, 3,5-dibromo-2-hydroxyacetophenone, 4-ethoxy-2-hydroxyacetophenone, 5-ethoxycarbonyl-ethoxy-2-hydroxyacetophenone, 4-methoxycarbonylmethoxy-2-hydroxyacetophenone, 4-carboxymethyl-2-hydroxyacetophenone, 5-nitro-2-hydroxyacetophenone, 3-cyano-2-hydroxyacetophenone, 4-trifluoromethyl-2-hydroxyacetophenone, 5-trifluoromethyl-2-hydroxyacetophenone, 3-trifluoromethyl-2-hydroxyacetophenone, 3-methoxycarbonyl-2-hydroxyacetophenone, 5-carboxy-2-hydroxyacetophenone, 4-amino-2-hydroxyacetophenone, 3-hexylamino-2-hydroxyacetophenone, 5-dimethylamino-2-hydroxyacetophenone, 4-N-piperidinyl-2-hydroxyacetophenone, 3-phenoxy-2-hydroxyacetophenone, 4-p-chlorophenoxy-2-hydroxyacetophenone, 5-p-tolyl-2-hydroxyacetophenone, 2-hydroxypropiophenone, 5-methyl-2-hydroxy-1-phenylacetyl-benzene, 2-hydroxy-ω-diethylaminoacetophenone, 2-hydroxy-ω-carboxybutyrophenone and 2-hydroxy-5-phenoxyacetophenone.

Preferred carbonyl compounds of the formula III, which can be employed according to the process of the invention, are compounds of the formula

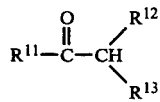
(VI)

wherein
$R^{11}$, $R^{12}$ and $R^{13}$ are identical or different and represent $C_1$ to $C_{18}$ alkyl, $C_1$ to $C_{18}$ alkenyl, $C_5$ and $C_6$ cycloalkyl, $C_5$ and $C_6$ cycloalkenyl, phenyl, $C_7$ to $C_{10}$ aralkyl, $C_2$ to $C_6$ dialkylamino or carboxyalkyl.

The carbonyl compounds which can be used for the process according to the invention are known. Examples which may be mentioned are: acetaldehyde, propionaldehyde, n-butyraldehyde, iso-butyraldehyde, heptanal, undecylenaldehyde, acetone, methyl ethyl ketone, undecan-2-one, heptadecan-2-one, octadecan-2-one, nonadecan-2-one, diethyl ketone, 6-methylhept-5-en-2-one, cyclobutanone, cyclopentanone, cycloheptanone, cyclooctanone, cyclododecanone, 6,10,14-trimethylpentadecan-2-one, 6,10,14-trimethylpentadeca-5,9,13-trien-2-one, N-methylpiperidinone, N-benzylpiperidinone, N-acetylpiperidinone, phenylacetone, hydrocinnamaldehyde, phenylacetaldehyde, tetral-2-one, indan-2-one, indan-1-one, 6-methoxytetral-2-one, 5-diethylaminopentan-2-one, 4-N-pyrrolidinylbutan-2-one, β-dimethylaminopropionaldehyde, 5-hydroxypentan-2-one, 4,4,4-trifluorobutan-2-one, 4-phenylbutan-2-one, 4-p-hydroxyphenylbutan-2-one, 4,4-dimethoxybutan-2-one, 1-acetoxyacetone, pyruvic acid ethyl ester, levulinic acid, 5-ketohexanecarboxylic acid, 6-ketoheptanecarboxylic acid, 6-aldohexanecarboxylic acid, α-acetylaminoacetone, 1,2,5,6-tetrahydrobenzaldehyde, 4-carboxycyclohexanone and 4-phenylcyclohexanone.

The amines which can be used for the process according to the invention are known. Examples which may be mentioned are: pyrrolidine, piperidine, N-methylpiperazine, morpholine, dimethylamine and diethylamine, preferably pyrrolidine.

In place of the carbonyl compounds corresponding to the formula III and the amines corresponding to the formula IV, it is also possible to employ secondary products of the two components in the process according to the invention. Examples of secondary products which may be mentioned are enamines of the formula

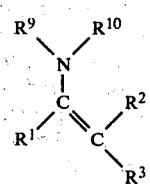
(VIII)

wherein
$R^1$, $R^2$, $R^3$, $R^9$ and $R^{10}$ have the abovementioned meaning,
and aminals of the formula

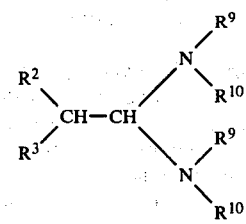
(IX)

wherein
$R^2$, $R^3$, $R^9$ and $R^{10}$ have the abovementioned meaning.

Examples of enamines which may be mentioned are: 1-pyrrolidinylhexene, 1-pyrrolidinyl-4-phenylcyclohexene, 1-pyrrolidinyl-4-ethylcyclohexene, 1-pyrrolidinylcyclohexene-4-carboxylic acid ethyl ester, 3-pyrrolidinylpent-2-ene, 1-pyrrolidinyl-cyclooctene, 1-pyrrolidinyl-cyclododecene, 2-pyrrolidinyl-1,3-diphenylpropene, α-[1-pyrrolidinylcyclohex-6-enyl]-propionic acid methyl ester, β-[1-pyrrolidinylcyclohex-6-enyl]-propionic acid isobutyl ester, β-[1-pyrrolidinylcyclohex-6-enyl]propionic acid methyl ester, β-[1-pyrrolidinylcyclohex-6-enyl]-propionic acid nitrile and 1-pyrrolidinylcyclohexene. They may be prepared according to G. Stork et al., J. Amer. Ch. Soc. 85, page 207 (1963).

Examples of aminals which may be mentioned are: 1,1-bis-(N-pyrrolidinyl)-butane and 1,1-bis-(N-piperidinyl)-hexane.

In order to carry out the process according to the invention, the o-hydroxycarbonyl compounds and the carbonyl compound, or the enamine or the aminal, are generally employed in equimolar amounts. However, for carrying out the process according to the invention, it is not significant if a relatively large excess of one component is employed.

The amount of amine employed is not critical. In general, 0.05 to 1.5 mols, preferably 0.1 to 1 mol, of the amine are used, based on 1 mol of the o-hydroxy-carbonyl compound. If the starting components are substituted by groups which have an acid reaction, such as, for example, carboxyl groups, it can be appropriate to neutralise the acid groups by means of an excess of the amine.

If, in place of the carbonyl compounds and amines, the corresponding enamines or aminals are used, it is indeed possible additionally also to employ a further amount of the corresponding amine or of another amine, but in general this is neither necessary nor appropriate.

A further possibility is not to employ the total equimolar amount of the carbonyl compound in the form of the enamine or aminal, but to employ in such a form only that part of the total amount which is equivalent to the about of amine selected for use, and to employ the carbonyl compound itself for the remainder of the total amount. For example, for one mol of the o-hydroxycarbonyl compound, 0.2 to 0.5 mol can be employed in the form of the enamine or aminal and 0.8 to 0.5 mol can be employed as the carbonyl compound itself.

As a result of the use of the corresponding enamines or aminals, it can be advantageous to employ 1 or 2 mols of the amine, based on 1 mol of the o-hydroxycarbonyl compound, but when the carbonyl compound itself is used it is also possible in many cases to use less amine, for example 0.2 to 0.5 mol of amine, with equal success.

The process according to the invention can be carried out at a temperature of $-30°$ to $+150°$ C., preferably of $10°$ to $120°$ C.

The pressure is not important for carrying out the process according to the invention. The process can be carried out under reduced, atmospheric or elevated pressure, preferably under atmospheric pressure.

The process according to the invention can be carried out with or without a solvent. Solvents which can be used for carrying out the process are those which are inert towards the starting components and the end product. Examples of solvents which may be mentioned are: aliphatic or aromatic hydrocarbons, such as petroleum ether, benzene, toluene or xylene, aliphatic or aromatic halogenated hydrocarbons, such as carbon tetrachloride, chlorobenzene or dichlorobenzene, ethers, such as diethyl ether, tetrahydrofurane, dioxane or glycol dimethyl ether, amides, such as dimethylformamide, dimethylacetamide and N-methylpyrrolidone, esters, such as ethyl acetate, nitriles, such as acetonitrile and propionitrile, and alcohols, such as methanol and ethanol, and glycol monomethyl ether.

In general, the process according to the invention may be carried out as follows:

The starting compounds are optionally dissolved in a solvent at the chosen reaction temperature and the amine is added. In general, the reaction temperature rises due to the exothermic reaction, so that further heating is not necessary. The reaction mixture is then left to stand, without further heating, until the reaction has ended.

In another reaction variant, the reaction mixture is heated to about 100° C. and the water of reaction is distilled off.

Subsequently, the amine and the solvent are separated off and the reaction mixture is distilled in order to isolate the desired chromanone derivative. The amine can be separated off by distillation or by extracting by shaking with aqueous acid, such as hydrochloric acid or sulphuric acid. It may be appropriate to carry out the distillation of the chroman-4-ones under reduced pressure and at a reduced temperature. In general, the boiling points of the chroman-4-ones are so high that a pressure of less than 10 mm Mg, preferably between 0.001 and 1 mm Mg, can appropriately be chosen for the distillation.

Of course, it is also possible to isolate and to purify the chroman-4-ones by other methods of working up which are in themselves known, as well as by distillation. For example, the reaction solution can be concentrated and the residue purified by recrystallisation.

The process according to the invention makes it possible to prepare chroman-4-ones in a simple manner and with high yields. Separating off the amine which has not been converted during the reaction is simple and makes it possible to use this compound repeatedly.

Advantageously, the process can be carried out without pollution of the environment due to unreacted compounds.

According to another aspect of the invention, there are provided chroman-4-ones of the formula

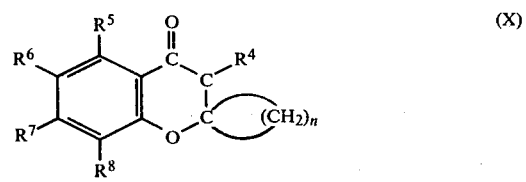

(X)

wherein
R$^4$ to R$^8$ have the abovementioned meaning and
m is a number from 4 to 12,
and of the formula

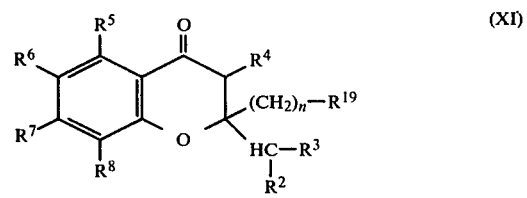

(XI)

wherein
R$^2$ to R$^8$ have the abovementioned meaning,
n is a number from 1 to 18 and
R$^{19}$ represents hydrogen, an amino, alkylamino or dialkylamino group or the group

—COOR$^{20}$ wherein
R$^{20}$ represents hydrogen or an alkyl radical,
and also of the formula

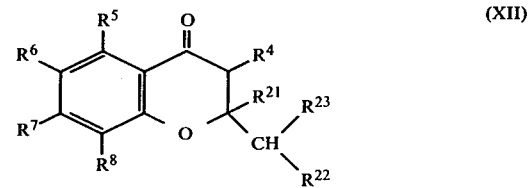

(XII)

wherein
R$^4$ to R$^8$ have the abovementioned meaning,
R$^{21}$ represents hydrogen or a C$_1$–C$_{18}$-alkyl group,
R$^{22}$ represents optionally substituted aryl, aralkyl or alkoxycarbonyl or represents dialkylamino or one of the groups

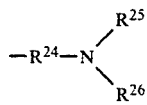

and —COOR$^{27}$
wherein
R$^{24}$ denotes alkylene and
R$^{25}$, R$^{26}$ and R$^{27}$ denote hydrogen or alkyl, and
R$^{23}$ represents hydrogen or alkyl, can be prepared by the process according to the invention.

A further preferred group of the chroman-4-ones according to the invention corresponds to the formula

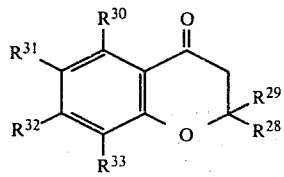

wherein
R$^{28}$ represents a C$_1$–C$_{18}$ alkenyl group or a C$_1$–C$_6$-alkylcarboxylic acid radical,
R$^{29}$ represents hydrogen or C$_1$–C$_6$-alkyl,
R$^{30}$ represents hydrogen or methyl,
R$^{31}$ represents hydroxyl, halogen or methyl and
R$^{32}$ and R$^{33}$ are identical or different and represent hydrogen or methyl.

Examples of new chroman-4-ones of the formula X which may be mentioned are: 2,2-tetramethylenechroman-4-one, 7-hydroxy-2,2-tetramethylenechroman-4-one, 6-hydroxy-2,2-tetramethylenechroman-4-one, 8-methoxy-2,2-tetramethylenechroman-4-one, 6-ethoxy-2,2-tetramethylenechroman-4-one, 7-benzyloxy-2,2-tetramethylenechroman-4-one, 7-chloro-2,2-tetramethylenechroman-4-one, 5-bromo-2,2-tetramethylenechroman-4-one, 5,7-dihydroxy-2,2-tetramethylenechroman-4-one, 6,8-dihydroxy-2,2-tetramethylenechroman-4-one, 5,8-dihydroxy-2,2-tetramethylenechroman-4-one, 5,7,8-trihydroxy-2,2-tetramethylenechroman-4-one, 5-hydroxy-7-pentyl-2,2-tetramethylenechroman-4-one, 5-hydroxy-7-pentyl-2,2-undecamethylenechroman-4-one, 2,2-pentamethylenechroman-4-one, 2,2-pentamethylene-7-hydroxychroman-4-one, 2,2-pentamethylene-6-hydroxychroman-4-one, 2,2-pentamethylene-6-methoxychroman-4-one, 2,2-pentamethylene-7-methoxychroman-4-one, 7-acetylamino-2,2-pentamethylenechroman-4-one, 6-cyclohexyl-2,2-pentamethylenechroman-4-one, 5-chloro-7-phenyl-2,2-pentamethylenechroman-4-one, 7-alkyloxy-2,2-pentamethylenechroman-4-one, 6-ethoxycarbonylmethoxy-2,2-pentamethylenechroman-4-one, 6-nitro-2,2-pentamethylenechroman-4-one, 5-cyano-2,2-pentamethylenechroman-4-one, 7-trifluoromethyl-2,2-pentamethylenechroman-4-one, 6-carboxy-2,2-pentamethylenechroman-4-one, 7-methoxycarbonyl-2,2-pentamethylenechroman-4-one, 6-butyramido-2,2-pentamethylenechroman-4-one, 7-amino-2,2-pentamethylenechroman-4-one and 5-hydroxy-7-pentyl-2,2-pentamethylenechroman-4-one.

Examples of new chroman-4-ones of the formula XI which may be mentioned are: 2-methyl-2-(δ-diethylaminopropyl)chroman-4-one, 2-methyl-2-(β-carboxyethyl)-chroman-4-one, 2-methyl-2-nonyl-7-hydroxy-chroman-4-one, 2-methyl-2-(β-N-pyrrolidinylethyl)-chroman-4-one, 2-methyl-2-(δ-carboxybutyl)chroman-4-one, 2-isopropyl-3-phenyl-6-methyl-chroman-4-one, 2,3,6-trimethyl-chroman-4-one, 6-dimethylamino-2-isopropylchroman-4-one, 7-acetamino-2-isopropyl-chroman-4-one, 7-chloro-2-propyl-chroman-4-one, 6-hexylamino-2-methyl-2-nonyl-chroman-4-one, 5-hydroxy-7-heptyl-2-methyl-2-nonyl-chroman-4-one, 5-methyl-7-hydroxy-2-methyl-2-δ-carboxybutyl-chroman-4-one, 6-hydroxy-2-methyl-2-δ-carboxybutyl-chroman-4-one, 7-hydroxy-2-δ-carboxybutyl-chroman-4-one, 5-hydroxy-7-pentyl-2-methyl-2-β-carboxyethyl-chroman-4-one, 6-hydroxy-2-methyl-2-β,β,β-trifluoroethyl-chroman-4-one, 7-hydroxy-2-methyl-2-diethylaminopropyl-chroman-4-one, 2-methyl-2-N-pyrrolidinylpropyl-chroman-4-one, 2-methyl-2-benzyl-chroman-4-one, 2-hydroxybutyl-chroman-4-one and 2,5,7,8-tetramethyl-6-hydroxy-2-(4′,8′,12′-trimethyl-trideca-3′,7′,11′-trienyl)-chroman-4-one [4-keto-α-tocotrienol].

The chroman-4-ones according to the invention have a pharmaceutical, insecticidal (see Chem. Eng. News, 1976, p, 19) and antioxidant action. They can advantageously be employed for material protection. Vitamin E (α-tocopherol) can be obtained from 2,5,7,8-tetramethyl-6-hydroxy-2-(4′,8′,12′-trimethyltrideca-3′,7′,11′-trienyl)-chroman-4-one [4-keto-α-tocotrienol] by reduction of the keto and olefine groups.

EXAMPLES 1 TO 30

Process A:
A mixture of 600 g of o-hydroxy-acetophenone, 1 l of methanol and 630 g of 1-N-pyrrolidinylcyclopentene is warmed to the reflux temperature for 2 hours and then concentrated. On fractional distillation, the residue gives, in addition to first runnings, 770 g (86% of the theoretical yield) of 2,2-tetramethylenechroman-4-one; boiling point 100°–105° C./0.05 mm Hg.

Process B:
100 g of pyrrolidine are added to a mixture of 680 g of o-hydroxy-acetophenone, 1½ l of toluene and 550 g of cyclopentanone, the mixture is left to stand for 1 day at 25° and is then heated for 5 hours under a water separator. After cooling, the organic phase is extracted by shaking with 250 ml of 2 N NaOH, 700 ml of 2 N HCL and 500 ml of water and the toluene solution is dried over sodium sulphate, concentrated and distilled. 860 g (85% of the theoretical yield) of 2,2-tetramethylenechroman-4-one are obtained at a boiling point of 110°–120° C. under 0.1 mm Hg.

The 2,2-tetramethylenechroman-4-ones obtained by the two variants are identical: they display the expected signals in the nuclear magnetic resonance spectrum and in the infrared spectrum show a strong band at 1,600–1,690 cm$^{-1}$.

The chroman-4-ones listed in the table which follows are prepared according to variant A or B.

According to variant A, one mol of a o-hydroxy-arylcarbonyl compound of the formula

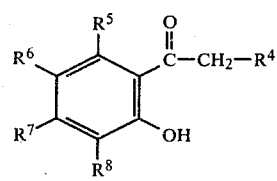

is reacted in 2.5 times the amount by volume of the indicated solvent with an enamine of the formula

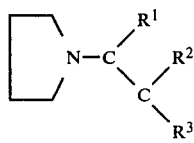

The particular substituents are indicated in the table which follows.

According to variant B, one mol of an o-hydroxy-aryl-carbonyl compound of the formula

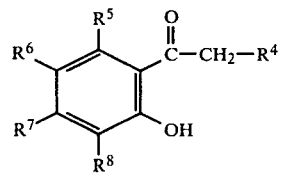

is reacted in 2.5 times the amount by volume of the indicated solvent with a carbonyl compound of the formula

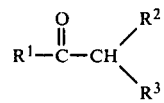

in the presence of pyrrolidine. The particular substituents are indicated in the table which follows. The molar amount of pyrrolidine, based on the o-hydroxy-arylcarbonyl compound, is also indicated in the table.

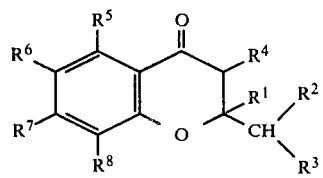

| Example | $R^1-R^8$ | Process | Solvent | Time/temperature | Amine (amount) | Yield | Boiling point/mm Hg (melting point) |
|---|---|---|---|---|---|---|---|
| 2 | $R^1 + R^2-(CH_2)_4-$ | A | Methanol | 24 hours/25° 2 hours/70° | | 89.3% | 130°/0.1 |
| 3 | $R^1 + R^2-(CH_2)_4-$ | B | Toluene | 6 hours/25° 2 hours/115° | Pyrrolidine (1 mol) | 74% | 140°/0.2 |
| 4 | $R^1 + R^2-(CH_2)_6-$ | A | Xylene | 3 hours/145° | | 20% | 170°/0.1 |
| 5 | $R^1 + R^2-(CH_2)_6-$ | B | Toluene | 6 hours/25° 5 hours/115° | Pyrrolidine (1 mol) | 67% | 170°/0.1 |
| 6 | $R^1 + R^2-(CH_2)_{10}-$ | B | Toluene | 20 hours/25° 2 hours/115° | Pyrilidine (1 mol) | 53% | 220°/0.1 [93-5°] |
| 7 | $R^1 + R^2-CH_2-CH_2-\underset{CH_3}{N}-CH_2$ | A | Methanol | 2 hours/70° | | 96% | 135°/0.1 |
| 8 | $R^1 + R^2-CH_2-CH_2-\underset{COOC_2H_5}{CH}-CH_2$ | A | Methanol | 24 hours/25° | | 55% | 190°/0.1 |
| 9 | $R^6-Cl; R^1 + R^2-(CH_2)_4-$ | A | Methanol | 24 hours/25° | | 72% | 155°/0.05 |
| 10 | $R^8-Cl; R^1 + R^2-(CH_2)_4-$ | A | Methanol | 24 hours/25° | | 69% | 160°/0.05 |
| 11 | $R^6-CH_3O-; R^1 + R^2-(CH_2)_4-$ | A | Methanol | 2 hours/70° | | 92% | 150°/0.05 |
| 12 | $R^8-CH_3O; R^1 + R^2-(CH_2)_4-$ | A | Methanol | 2 hours/70° | | 84% | 165°/0.05 |
| 13 | $R^2, R^3-CH_3$ | A | Methanol | 20 hours/25° | | 91% | 110°/0.1 |
| 14 | $R^2, R^3-CH_3$ | B | Toluene | 2 hours/115° | Pyrrolidine (1 mol) | 93% | 110°/0.1 |
| 15 | $R^2-CH_2-\langle\!\!\!\!\bigcirc\!\!\!\!\rangle-$ | A | Methanol | 2 hours/70° | | 15% | (118-20°) |
| 16 | $R^2, R^3-CH_3; R^4-CH_3; R^7-Cl$ | A | Toluene | 2½ hours/100° | | 70% | 130°/0.1 |
| 17 | $R^1 + R^2-(CH_2)_4-$ $R^7-C_6H_3CH_2O-$ | A | Methanol | 24 hours/25° | | 85% | (100-102°) |
| 18 | $R^2, R^3, R^6-CH_3; R^4-C_6H_5$ | A | without solvent | 3 hours/120° | | 71% | (75-6°) |
| 19 | $R^1-CH_3$ | B | Toluene | 5 hours/25° 2 hours/80° | Pyrrolidine (1 mol) | 50% | (88-9°) |
| 20 | $R^2-C_6H_3-CH_2$ | B | Toluene | 20 hours/25° 1 hour/115° | Pyrro- (1 mol) lidine (0.1 mol) | 56% 34% | 185°/0.1 |
| 21 | $R^1-C_6H_5-CH_2$ | B | Toluene | 2 hours/110° | Pyrrolidine (1 mol) | 35% | 155°/0.1 |

-continued

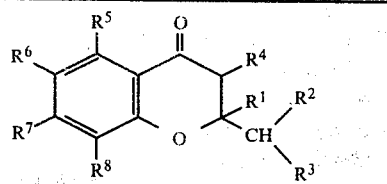

| Example | $R^1$—$R^8$ | Process | Solvent | Time/temperature | Amine (amount) | Yield | Boiling point/mm Hg (melting point) |
|---|---|---|---|---|---|---|---|
| 22 | $R^2$—$C_2H_5$ | B | Toluene | 5 hours/25° 2 hours/reflux | Pyrrolidine (1 mol) | 48% | 120°/0.05 |
| 23 | $R^1$—$C_6H_5$ | B | Toluene | 5 hours/105° | Pyrrolidine (1 mol) | 14% | 160°/0.1 |
| 24 | $R^2$-n-pentyl | B | Toluene | 2 hours/110° | Pyrrolidine (1 mol) | 52% | 155°/0.1 |
| 25 | $R_1$-n-nonyl | B | Toluene | 2 hours/110° | Pyrrolidine (1 mol) | 63% | 175°/0.07 |
| 26 | $R^1$—$CH_2$—$CH_2$—$N(C_2H_5)_2$ | B | Toluene | 4 hours/110° | Pyrrolidine (0.3 mol) | 49% | 180°/0.2 |
| 27 | $R^1 + R^2$—$(CH_2)_3$ | B | Toluene | 20 hours/25° 2 hours/105° | Pyrrolidine (0.2 mol) | 41% | 210°/0.2 |
| 28 | $R^7$—$C_2H_5OOC$—$CH_2O$— $R^1$—$(CH_2)_4$—$COOH$ | B | Toluene | 24 hours/25° 2 hours/105° | Pyrrolidine (1.2 mols) | 46% | 205°/0.1 |
| 29 | $R^1$-n-nonyl; $R^7$—OH | B | Toluene | 24 hours/25° 2 hours/105° | Pyrrolidine | 42% | 240°/0.1 |
| 30 | $R^1$—$CH_2$—$COOC_2H_5$ | A | without solvent | 2 hours/180° | | 25% | 195°/0.1 |

EXAMPLE 31

304 g of 2,4-dihydroxy-acetophenone and 142 g of pyrrolidine are stirred in 1 l of toluene. 320 g of 1-N-pyrrolidinyl-cyclohexane are then added and the mixture is stirred for 3 hours at 25° and then for a further 3 hours at the reflux temperature. After cooling, 1 kg of ice and 1 l 4 N HCl are stirred into the dark solution. After a short time 2,2-pentamethylene-7-hydroxychroman-4-one precipitates out from the organic phase and is filtered off and rinsed with water. The toluene is separated off from the filtrate and concentrated to about 400 ml, whereupon a further fraction precipitates. Total yield 339 g (73% of the theoretical yield): melting point: 170°–171°.

EXAMPLE 32

41 g of o-hydroxyacetophenone, 100 ml of toluene and 51 g of 1-N-piperidinyl-cyclohexene are warmed to 115° C. for 5 hours. After cooling, the solution is extracted by shaking with 200 ml of 2 N HCl and with water and the organic phase is dried over sodium sulphate, concentrated and distilled. 36 g (56% of the theoretical yield) of 2,2-pentamethylene-chroman-4-one (boiling point: 130°/0.05), which is identical to the product obtained in Examples 2 and 3, are obtained.

EXAMPLE 33

24 g of pyrrolidine are added carefully, at under 30°, to a solution of 41 g of o-hydroxyacetophenone, 25 g of levulinic acid and 100 ml of toluene. The mixture is left to stand for 3 days at 25° and the solution is extracted by shaking with 150 ml of concentrated sodium carbonate solution. The aqueous phase is acidified with 2 N HCl and then extracted by shaking with ether. The ethereal solution is concentrated and distilled, 14 g (20% of the theoretical yield) of 2-methyl-2-β-carboxyethyl-chroman-4-one being obtained: boiling point: 230°/0.1 mm Hg.

EXAMPLE 34

A mixture of 40 g of 2,5-dihydroxy-3,4,6-trimethylacetophenone, 55 g of farnesylacetone, 150 ml of toluene and 20 g of pyrrolidine is stirred for one day at 25° C. and then for 4 hours at the reflux temperature under a water separator. After cooling, the reaction mixture is treated with 150 ml of 2 N HCl and stirred for a further one hour. After it has settled out, the organic phase is separated off, washed with water and dried over sodium sulphate.

After distilling off the solvent, 65 g (73% of theory) of 2,5,7,8-tetramethyl-6-hydroxy-2-(4′,8′,12′-trimethyl-trideca-3′,7′,11′-trienyl)-chroman-4-one [4-keto-α-tocotrienol] are obtained in the boiling range from 270° to 275° C./0.1 mm Hg by fractional distillation.

EXAMPLE 35

After standing for 1 day at 25° C., a solution of 68 g of 5-chloro-2-hydroxy-acetophenone, 60 g of 5-ketohexanecarboxylic acid, 150 ml of toluene and 40 g of pyrrolidine is heated at the reflux temperature under a water separator for 2½ hours. After cooling, the mixture is acidified to pH=1 with 2 N HCl, whereupon an oily organic phase separates out. After separating this from the aqueous solution, the oil is distilled.

76 g (64% of theory) of 2-methyl-2-(4′-carboxybutyl)-6-chloro-chroman-4-one are obtained in the boiling range from 240° to 245° C./0.15 mm Hg.

EXAMPLE 36

A solution of 80 g of 2,5-dihydroxy-3,4,6-trimethylacetophenone, 112 g of 6,10,14-trimethylpentadecan-2-one, 250 ml of toluene and 50 ml of pyrrolidine is stirred for one day at 25° C. and then for 4 hours at the reflux temperature under a water separator. After cooling, the reaction mixture is treated with 150 ml of 2 N HCl and stirred for a further one hour. After it has settled out, the organic phase is separated off, washed with water and dried over a dium sulphate.

After distilling off the solvent, 147 g (82% of theory) of 2,5,7,8-tetramethyl-6-hydroxy-2-(4',8',12'-trimethyl-tridecanyl)-chroman-4-one (4-keto-α-tocopherol, 4-keto-vitamin E) are obtained in the boiling range from 275° to 280° C./0.12 mm Hg by fractional distillation.

What is claimed is:

1. Process for preparing a chroman-4-one of the formula

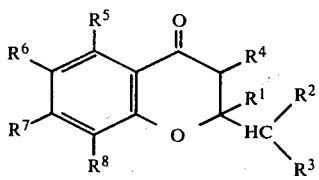

wherein $R^1$ to $R^3$ are identical or different and represent hydrogen, alkyl having up to 18 cabon atoms, alkenyl having up to 18 carbon atoms, cycloalkyl having 3 to 18 carbon atoms, cycloalkenyl having 3 to 18 carbon atoms, aryl having 6 to 14 carbon atoms, aralkyl having 7 to 18 carbon atoms with 1 to 8 carbon atoms in the aliphatic part, alkoxycarbonyl having up to 4 carbon atoms in the alkyl part of carboxyl or $C_2$ to $C_6$ carboxyalkyl, $R^1$ and $R^2$ can be closed to form a 3-membered to 12-membered carbocyclic ring or a 5- to 12-membered heterocyclic ring in which the hetero atoms are nitrogen, oxygen or sulfur, $R^4$ represents hydrogen, $R^5$ to $R^8$ are identical or different and represent hydrogen, halogen, hydroxyl, nitro, cyano, carboxyl, alkyl having up to 18 carbon atoms, cycloalkyl having 3 to 18 carbon atoms, aryl having 6 to 14 carbon atoms, aralkyl having 7 to 18 carbon atoms with 1 to 8 carbon atoms in the aliphatic part, alkoxy having up to 4 carbon atoms, aralkoxy having 7 to 10 carbon atoms, aryloxy having 6 to 10 carbon atoms, alkoxycarbonyl having up to 4 carbon atoms in the alkyl part, and acylamino having up to 18 carbon atoms, and wherein each of said alkyl, cycloalkyl, aryl, aralkyl, alkoxy, aralkoxy or alkoxycarbonyl is substituted by substituents which are inert under the reaction conditions, which comprises reacting an o-hydroxy-arylcarbonyl compound of the formula

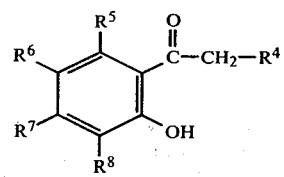

wherein $R^4$ to $R^8$ have the above-mentioned meaning, with carbonyl compound of the formula

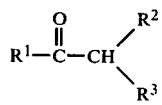

wherein $R^1$ and $R^3$ have the above-mentioned meaning, in the presence of an amine of the formula

wherein $R^9$ and $R^{10}$ represent alkyl groups having up to 18 carbon atoms which, together with the N atom, can be linked to form a heterocyclic ring having 5 to 6 ring members.

2. Process of claim 1 wherein the alkyl and alkenyl radicals are straight-chain or branched radicals with up to 12 carbon atoms, the cycloalkyl radicals have 4 to 12 carbon atoms, the cycloalkenyl radicals are 5- or 6-membered alicyclic radicals each having a double bond, the aryl radicals have 6 to 14 carbon atoms, and the aralkyl radicals have 7 to 18 carbon atoms with 1 to 4 carbon atoms in the aliphatic part and 6 to 10 carbon atoms in the aromatic part.

3. Process of claim 1 wherein $R^1$ and $R^2$ together represent a saturated or unsaturated 3 to 12 membered carbocyclic ring, or a 5 to 12 membered heterocyclic ring.

4. Process of claim 1 wherein the e-hydroxyarylcarbonyl compound has the formula

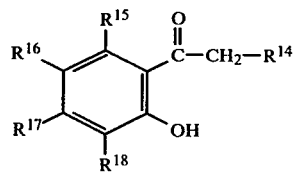

wherein $R^{14}$ represents hydrogen, and $R^{15}$ to $R^{18}$ are identical or different and represent hydrogen, chlorine, bromine, hydroxyl, $C_1$ to $C_6$ alkyl, phenyl, $C_1$ to $C_6$ alkoxy, $C_7$ to $C_9$ aralkoxy.

5. Process of claim 1 wherein the carbonyl compound has the formula

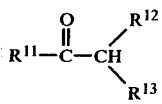

wherein $R^{11}$, $R^{12}$ and $R^{13}$ are identical or different and represent $C_1$ to $C_{18}$ alkyl, $C_1$ to $C_{18}$ alkenyl, $C_3$ and $C_6$ cycloalkyl, $C_5$ and $C_6$ cycloalkenyl, phenyl, $C_7$ to $C_{10}$ aralkyl.

6. Process of claim 11 wherein the amine is pyrrolidine, piperidine, N-methylpiperasine morpholine, dimethylamine or diethylamine.

7. Process of claim 1 wherein in place of the carbonyl compound and the amine, an enamine of the formula

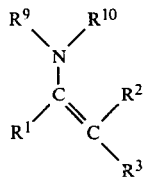
wherein
$R^1$, $R^2$, $R^3$, $R^9$ and $R^{10}$ have the meaning indicated in claim 1
is employed.
8. Process of claim 1 wherein the reaction is carried out at a temperature of $-30°$ to $+150°$ C.
9. Process of claim 8 wherein the temperature is 10° to 120° C.
10. Process of claim 1 wherein the reaction is carried out at atmospheric pressure.
11. Process of claim 1 wherein an inert solvent is present.
* * * * *